United States Patent
Schmidt et al.

(10) Patent No.: US 6,391,560 B1
(45) Date of Patent: May 21, 2002

(54) SCREENING FOR FUNCTIONAL ANTISENSE AGENTS

(75) Inventors: Gunter Schmidt, Cambridge; Andrew Hugin Thompson, Ayr, both of (GB)

(73) Assignee: Brax Group Limited, Cambridge (GB)

( * ) Notice: Subject to any disclaimer, the term of this patent is extended or adjusted under 35 U.S.C. 154(b) by 0 days.

(21) Appl. No.: 09/623,390

(22) PCT Filed: Mar. 3, 1999

(86) PCT No.: PCT/GB99/00630

§ 371 Date: Mar. 26, 2001

§ 102(e) Date: Mar. 26, 2001

(87) PCT Pub. No.: WO99/45144

PCT Pub. Date: Sep. 10, 1999

(30) Foreign Application Priority Data

Mar. 3, 1998 (GB) .............................................. 9804524

(51) Int. Cl.[7] .................................................. C12Q 1/68
(52) U.S. Cl. .......................................................... 435/6
(58) Field of Search ............................................. 435/6

(56) References Cited

U.S. PATENT DOCUMENTS 5,686,242 A    11/1997  Bruice et al. .................. 435/6
6,194,149 B1 *  2/2001  Neri et al. ...................... 435/6

FOREIGN PATENT DOCUMENTS

WO    WO97/10332    3/1997

OTHER PUBLICATIONS

Stimpson, Don et al., "Real–time detection of DNA hybridization and melting on oligonucleotide arrays by using optical wave guides" *Proc. Natl. Acad. Sci. USA*, vol. 92, (Jul. 1995) pp. 6379–6383.

Kenrick, Michael K. et al., "A homogeneous method to quantify mRNA levels: a hybridization of RNase protection and scintillation proximity assay technologies" *Nucleic Acids Research*, vol. 25, No. 14 (1997) p. 2947–2948.

Ho, Siew Peng et al., "Potent antisense oligonucleotides to the human multidrug resistance–1 mRNA are rationally selected by mapping RNA–accessible sites with oligonucleotide libraries" *Nucleic Acids Research*, vol. 24, No. 10 (1996) pp. 1901–1907.

Kronenwett, Ralf et al., "Kinetic Selectivity of Complementary Nucleic Acids: bcr–abl–directed Antisense RNA and Ribozymes" *J. Mol. Biol.*, vol. 259 (1996) pp. 632–644.

\* cited by examiner

Primary Examiner—Kenneth R. Horlick
Assistant Examiner—Teresa Strzelecka
(74) Attorney, Agent, or Firm—Robin L. Teskin

(57) ABSTRACT

Provided is a method for identifying a functional antisense agent, which method comprises contacting an RNA with an oligonucleotide probe to form a duplex-containing RNA, contacting the duplex-containing RNA with an RNAase to cleave the duplex-containing RNA, and measuring the kinetics of cleavage.

21 Claims, No Drawings

SCREENING FOR FUNCTIONAL ANTISENSE AGENTS

The present application concerns methods for the identification of functional antisense agents. In particular, the present application is concerned with improved methods for measuring the effectiveness of potential antisense oligonucleotides, via the kinetics of RNA/oligonucleotide hybrid cleavage.

PCT/GB96/02275 describes a method to determine which oligonucleotides, in a library, are active antisense agents, by identification of the sites at which cleavage of a target RNA occurs. The methods of this invention do not identify which of the oligonucleotides in the library of this invention is likely to be the most effective antisense agent.

PCT/GB97/02722 describes a method to identify which regions of an RNA are accessible to hybridisation probes by hybridising short oligonucleotide probes to a target RNA in separate reactions. The sequences of the hybridising probes are compared with the primary sequence of the target RNA to identify probes which hybridise to overlapping sequences in the target RNA. These sequences identify accessible regions in the target RNA. The methods in this application do not determine whether oligonucleotides complementary to an accessible site in a target RNA will mediate cleavage of that RNA by RNAse H.

It is an object of this invention to solve the problems arising from deficiencies in the above prior art methods and to provide a method of determining which oligonucleotides in an array of short oligonucleotide probes are most effective at mediating cleavage of a target RNA by RNAse H. It is also an object of this invention to compare this cleavage data with the primary sequence of the target RNA to identify contiguous sequences within the mRNA that are most accessible to oligonucleotides which can mediate RNAse H cleavage of the target. This will allow antisense agents, of sufficient length to be highly target specific, to be identified using a generic library of oligonucleotide probes that can be used to analyse any target RNA It is a further object of this invention to provide methods of identifying effective antisense agents that meet the earlier objectives without requiring gel electrophoresis or related separation techniques.

Accordingly, this invention provides a method for identifying a functional antisense agent, which method comprises contacting an RNA with an oligonucleotide probe to form a duplex-containing RNA, contacting the duplex-containing RNA with an RNAase to cleave the duplex-containing RNA, and measuring the kinetics of cleavage.

The invention also provides a kit for identifying a functional antisense agent, which kit comprises an oligonucleotide probe, an RNAase and a means for generating a signal for measuring the kinetics of cleavage of a duplex-containing RNA.

In this invention contacting can mean adding one reagent to a second reagent or vice versa. Thus, the RNAase can be added to the RNA before or after adding the oligonucleotide probe to the RNA.

A particularly preferred method of this invention is a method comprising the following steps of:

1. Preparing a pure sample of a labelled target RNA with an immobilisation agent that will allow the target RNA to captured onto a solid phase support. The label is preferably attached to the target RNA at the opposite terminus of the RNA from the immobilisation effector.
2. Immobilising the labelled target RNA in an array of wells so that, preferably, the same quantity of target RNA is captured in each well.
3. Incubating a single oligonucleotide probe from an array of oligonucleotides with the target RNA in each well in the presence of RNAse H. A different oligonucleotide probe from the array is incubated with the target RNA in each well.
4. Either:
    Determining the quantity of RNA cleaved in each well after a fixed period of time, by washing away cleaved RNA, enzyme, buffers and oligonucleotide probes and measuring how much labelled RNA remains in each well; (these steps 1 to 4 may be repeated with the washing step being performed after varying incubation times to determine a time course for the cleavage reaction)
    Or:
    Recording in real time the loss of signal from the labelled RNA, using an appropriate labelling system where the signal from the label is lost or reduced after cleavage of the labelled RNA.
5. Comparing the primary sequence of the target RNA with the sequences of the probes that mediate cleavage with the fastest kinetics to identify regions of the target RNA which are accessible to RNAse H mediated antisense cleavage agents.

Generating Immobilised Target RNAs

An important feature of this invention is capturing a labelled target RNA onto a solid phase support. Certain target RNAs will be derived from poly-adenylated messenger RNA. Target RNA of this kind could be captured using a poly-thymidine oligonucleotide immobilised on a solid phase support. The hybridisation can be reinforced with a covalent linkage if psoralen is included as part of the poly-T capture oligonucleotide. Psoralen can be photoactivated to cross-link to appropriate functional groups close in space.

If the primary sequence of an RNA is known, a short oligonucleotide can be synthesised that is complementary to some part of that primary sequence. It is preferable that this oligonucleotide be complementary to a region at the 3' or 5' terminus of the target to minimise disruption of the tertiary structure of the molecule. The capture oligonucleotide can be chemically synthesised with a capture agent such as biotin to allow it to be immobilised on a solid phase support.

A short oligonucleotide can be ligated onto one terminus of the target RNA to allow the RNA to be captured by the complementary oligonucleotide which may be immobilised on a solid phase support. This approach is a preferred approach as a generic pair of capture oligonucleotides can be used for all RNA targets. As a variant of this technique, an expression vector can be constructed which provides a capture sequence flanking the integration site for the sequence to be expressed as a target RNA. The flanking sequence is expressed with the integrated target sequence allowing it to be captured using a generic probe sequence.

Another preferred method uses terminal transferases to add biotinylated bases to one terminus of a target RNA allowing it to be immobilised on a solid phase support derivitised with avidin.

Reporter Groups to Permit Real Time Kinetic Analysis of Cleavage

Incubation times of the cleavage reaction of this invention can be varied to derive kinetic data about each cleavage reaction. The amount of immobilised RNA that has been cleaved after a given time will give quantitative data about the rate of the cleavage mediated by a particular probe for its target. By varying the incubation times for the cleavage reactions, a time course for the hybridisation reaction can be derived. The accessibility of any region of the structure will be inversely related to the time its complementary probe will take to bind and thus mediate RNAse H cleavage of the resultant duplex. It is desirable to analyse the cleavage reaction in real time to allow detailed information about the kinetics of the cleavage mediated by each probe in the array of this invention.

Radio-isotopes

Radiolabelling may be used in order to determine the kinetics of a cleavage reaction in real time, particularly using radio-isotopes that produce low energy radiation with short path lengths such as $^{33}$P. The radiation emitted by a radio-label can be detected by various means, including measuring scintillation or by Geiger counters. The intensity measured is determined by the distance of the radiation source from the detector. The further from the source the lower the intensity that is measured. If an RNA molecule is labelled with $^{33}$P, and immobilised on a scintillant containing surface, one would expect a relatively constant scintillation count which is indicative of the amount of RNA present at the surface of the plate. If this labelled target RNA is then incubated with an oligonucleotide probe of this invention in the presence of RNAse H, the scintillation count from RNA immobilised at the scintillant surface decreases as the labelled RNA is cleaved by RNAse H. The rate at which the scintillation count decreases is a measure of the rate of the cleavage reaction occurring. One would expect there to be a background count, from molecules free in solution close enough to the scintillant surface to be detected, so control reactions must be performed with labelled RNA free in solution. In this sort of system, spatial resolution of probes is essential, as only one radiolabel can be used at a time, so only one probe or RNA could be labelled at a time. The primary benefit of a system based on radiolabelling is the ability to measure cleavage reactions in real time to give detailed kinetic data. Real time analysis can be achieved by detecting scintillation with a photoamplification and detection system coupled to appropriate signal processing electronics such as the Amersham Cytostar-T scintilling microplates.

Scattering of Evanescent Waves from Optical Wave Guides

A non-radioactive method to determine the kinetics of a cleavage reaction in real time would be preferable to radio-labelling for safety reasons. A method of measuring the kinetics of nucleic acid hybridisation is described by D. I. Stimpson et al in Proc. Natl. Acad. Sci. USA, 92: 6379–6383, 1995. The method disclosed in this publication measures the hybridisation of a labelled oligonucleotide probe to a target immobilised at the surface of an optical wave guide. An optical wave guide transmitting light produces an 'evanescent wave' which extends some distance above the surface of the wave guide. Light from the evanescent wave can be scattered by a particulate label near the surface of the wave guide. This scattered light can be detected by a Charge Coupled Device camera. The quantity of scattered light is a measure of the quantity of particulate label near the surface of the wave guide. The evanescent wave extends only about 100 to 300 nm beyond the surface of the wave guide so only labelled material close to the surface of the wave guide will scatter light. This is ideal for measuring binding, unbinding or cleavage events close to the surface of the wave guide as a binding reaction at the surface of the wave guide will greatly increase the quantity of labelled probe within the evanescent wave over the background present free in solution. If a target RNA molecule is labelled with an appropriate particulate label the methods of the above publication could be applied with the methods of this invention. In the above publication by Stimpson et al, 200 nm selenium particles were conjugated with an anti-biotin antibody and linked to biotinylated oligonucteotide probes. Biotinylation of one terminus of a target RNA would allow a similar label to be used with this invention, but an alternative capture mechanism would be required to immobilise the target RNA at the surface of a waveguide by its other terminus. If an RNA labelled in this way were immobilised at the surface of a waveguide, a constant scattering of light should occur indicating the quantity of RNA immobilised. If this labelled target RNA were then incubated with an oligonucleotide probe of this invention in the presence of RNAse H, one would expect the quantity of light scattered from the surface of the wave guide to decrease as the labelled RNA is cleaved by RNAse H. The rate at which the scattering of light from the surface of the wave guide decreases is a measure of the rate of the cleavage reaction occurring. One would expect there to be a background count, from labelled RNA fragments free in solution close enough to the wave guide surface to be detected, so control reactions must be performed with labelled RNA free in solution.

Structure of Oligonucleotide Probes

The methods of this invention would become impractical if large oligonucleotides (ONs) were used as the behaviour of each ON is screened independently and the number of screening reactions increase as $N^4$ where N is the length of the probe. The ONs of this invention do not need to occur uniquely in their target RNA and so they can be fairly short. A probe length of 6 nucleotides is thought to be the minimum size recognised by RNAse H, but other RNAases exist which recognise nucleic acids as short as 4 bases in length. Oligonucleotides of preferably 4 or more nucleotides in length, more preferably 6–8 nucleotides in length can be used in this approach. Preferred libraries of ONs for use with this invention have a fixed length and contain all sequences of that length, although not every sequence in the library need be resolved from every other. Certain specific ONs might show some cross-hybridisation in this embodiment, but since individual ONs are screened separately these problems should be controllable.

There are two major factors that must be considered when using relatively short oligonucleotide probes. Short oligonucleotide probes have relatively low melting temperatures, although RNA/DNA hybrids have higher binding energies than RNA/RNA or DNA/DNA duplexes. To ensure that the hybridisation of probe to an immobilised RNA is strong enough, one requires that the oligonucleotides be long enough to ensure a reasonable degree of hybridisation but the longer the probe the more massive the task of resolving the behaviour of individual library members.

One can overcome the problem of weak hybridisation of short oligonucleotides indirectly by constructing oligonucleotides in sets such that each set is composed of a fixed number of bases of known sequence flanked on one side, or other, or both, by a further fixed number of bases such that all possible combinations of bases are represented in these flanking sequences:

5'-NNXXXXNN-3'

The above example has 2 bases, labelled N for any base, flanking the known 4 sequence 'window', XXXX, on both sides. Thus a preferred array of probe oligonucleotides for use with this invention comprises 256 different sets of 8-mers, where the central 4 bases in each set are known but where the flanking sequences contain all possible bases, which can be used to probe the immobilised RNA. This is effectively the same as probing with 4-mers but the flanking bases would increase the stability of interactions. The stability of interactions between probes of the library and a target RNA can be increased further by synthesising the probes of the invention with certain non-natural nucleic acid analogs. The use of flanking sequences is also preferable to ensure probe oligonucleotides of this invention are long enough to mediate cleavage by RNAse H.

Preferably the probes described above are chimeric, where the flanking regions of the probes are synthesised with backbones that are not recognised by RNAse H while the internal bases are synthesised with backbones that are recognised by RNAse H. Backbones that are not recognised by RNAse H include methyl-phosphonates and Peptide Nucleic Acid (PNA) backbones. Backbones that are recognised by RNAse H include phosphorothioates and natural phosphodiesters. The advantage of synthesising chimeric probes of this form is that they will limit the activity of RNAse H to the known bases of the probe reducing any artefacts that might be introduced by the flanking regions. In addition, it is desirable that the probes be synthesised from analogues that are exonuclease resistant, or that at least the flanking bases are synthesised from nucleic acid analogues that are exonuclease resistant.

The preferred length of probe 'window' is 4 bp. These might appear frequently in an RNA, as there are likely to be more than 2 occurrences of any given 4-mer present in a single RNA. Resolving the behaviour of 4-mer probes that occur more than once is however simplified in that a large proportion of any given RNA will be sequestered in secondary and tertiary structure. Moreover the kinetics of hybridisation of 4-mers complementary to regions adjacent in the primary sequence should be similar if the accessibility of the binding sites are similar, which will aid interpretation of hybridisation data Using 5-mers or 6-mers as windows, with stabilising flanking regions, will be easier to resolve, when automated systems are available to cope with the added labour as these are more likely to appear only once in any given RNA. The preferred length of flanking sequences is 1 to 2 bases on both flanks of each probe.

Synthesis of Oligonucleotide Probes
Linking Reporter Groups to Nucleic Acids

Reporter and their linkers can be attached to a nucleic acid molecule at a number of locations in the nucleic acid. For conventional solid phase synthesisers the 5' hydroxyl of the sugar is the easiest to derivitise. Other favoured positions for modifications are on the base at the 5' position in the pyrimidines and the 7' and 8' positions in the purines. These are the preferred positions to attach reporter groups.

The 2' position on the sugar is accessible for attachment of a reporter group but is more appropriate for small mass modifications that are not to be removed.

The phosphate linkage in natural nucleic acids can be modified to a considerable degree as well permitting attachment of reporter groups.

Hybridisation Probes

Depending on the application, one might wish to use modified nucleic acid probes containing a number of different analogues. Analogues are known in the art which can be used to vary the hybridisation behaviour of probes containing them. There are also analogues which can increase resistance of probes to enzymatic degradation. Determining the melting temperature of hybridisation probes is particularly important when groups of hybridisation probes are to be used simultaneously. It may be desirable to modify the hybridisation behaviour of a group of probes so that the melting temperatures of the correctly hybridised probes are very close together or are at least above some threshold. Preferably the melting temperature of incorrectly hybridised probes will fall well below this threshold. This allows groups of probes to be used simultaneously whilst ensuring the stringency of hybridisation reactions.

There are major differences between the melting temperatures of short oligonucleotide duplexes containing all Watson-Crick base pairs. For example, duplexes comprising only adenine and thymine have much lower melting temperatures relative to duplexes containing only guanine and cytosine. These differences in stability can present problems when trying to hybridise mixtures of short oligonucleotides to a target RNA. Low temperatures are needed to hybridise A-T rich sequences but at these temperatures G-C rich sequences will hybridise to sequences that are not fully complementary. This means that some mismatches may happen and specificity can be lost for the G-C rich sequences. At higher temperatures G-C rich sequences will hybridise specifically but A-T rich sequences will not hybridise.

In order to normalise these effects modifications can be made to nucleic acids. Modifications fall into three broad categories: Base modifications, Backbone modifications and Sugar modifications.

Base Modifications

Numerous modifications can be made to the standard Watson-Crick bases. The following are examples of modifications that could be used to normalise base pairing energies to some extent but they are not limiting:

The adenine analogue 2,6-diaminopurine forms three hydrogen bonds to thymine rather than two and therefore forms more stable base pairs.

The thymine analogue 5-propynyl dU forms more stable base pairs with adenine.

The guanine analogue hypoxanthine forms two hydrogen bonds with cytosine rather than three and therefore forms less stable base pairs.

These and other possible modifications make it possible to compress the temperature range at which short oligonucleotides can hybridise specifically to their complementary sequences.

Backbone Modifications

Nucleotides may be readily modified in the phosphate moiety. Under certain conditions, such as low salt concentration, analogues such as methylphosphonates, triesters and phosphoramidates have been shown to increase duplex stability. Such modifications may also have increased nuclease resistance. Further phosphate modifications include phosphodithirates and boranophosphates, each of which increase the stability of oligonucleotide against exonucleases.

Isosteric replacement of phosphorus by sulphur gives nuclease resistant ONs (reference 7). Replacement by carbon at either phosphorus or linking oxygen is also a further possibility.

Sugar Modifications

Various modifications to the 2' position in the sugar moiety may be made (references 12 and 13). The sugar may be replaced by a different sugar such as hexose or the entire sugar phosphate backbone can be entirely replaced by a novel structure such as in peptide nucleic acids (PNA). For a discussion see reference 8. PNA forms duplexes of the highest thermal stability of any analogues so far discovered.

Hydrophobic Modifications

Addition of hydrophobic groups to the 3' and 5' termini of an oligonucleotide also increase duplex stability by excluding water from the bases, thus reducing 'fraying' of the complex, i.e. hydrophobic groups reduce solvation of the terminal bases.

Hybridisation Protocols

Details on effects of hybridisation conditions, particularly buffers and temperature, for nucleic acid probes can be found in be found in references 9 to 11.

Oligonucleotide Synthesis

Methods of synthesis of oligonucleotides are well known in the art. The following are appropriate textbooks.

Gait, M. J. editor, 'Oligonucleotide Synthesis: A Practical Approach', IRL Press, Oxford, 1990

Eckstein, editor, 'Oligonucleotides and Analogues: A Practical Approach', IRL Press, Oxford, 1991

Liquid Handling Robotics

For this process to be useful on a practical commercial level, automation is preferred and liquid handling robots can be acquired from various sources such as Applied Biosystems Inc.

REFERENCES (1) Gait, M. J. editor, 'Oligonucleotide Synthesis: A Practical Approach', IRL Press, Oxford, 1990
(2) Eckstein, editor, 'Oligonucleotides and Analogues: A Practical Approach', IRL Press, Oxford, 1991
(3) Kricka, editor, 'Nonisotropic DNA Probe Techniques', Academic Press, San Diego, 1992
(4) Haugland, 'Handbook of Fluorescent Probes and Research Chemicals', Molecular Probes, Inc., Eugene, 1992
(5) Keller and Manack, 'DNA Probes, 2nd Edition', Stockton Press, New York, 1993
(6) Kessler, editor, 'Nonradioactive Labeling and Detection of Biomolecules', Springer-Verlag, Berlin, 1992.
(7) J. F. Milligan, M. D. Matteucci, J. C. Martin, J. Med. Chem. 36(14), 1923–1937,1993.
(8) P. E. Nielsen, Annu. Rev. Biophys. Biomol. Struct. 24, 167–183, 1995.
(9) Wetmur, Critical Reviews in Biochemistry and Molecular Biology, 26, 227–259, 1991
(10) Sambrook et al, 'Molecular Cloning: A Laboratory Manual, 2nd Edition', Cold Spring Harbour Laboratory, New York, 1989
(11) Harnes, B. D., Higgins, S. J., 'Nucleic Acid Hybridisation: A Practical Approach', IRL Press, Oxford, 1988

What is claimed is:

1. A method for identifying a functional antisense agent, which method comprises:
   a) contacting an RNA attached to a solid support with one or more arrays of oligonucleotides to form a duplex-containing RNA, each oligonucleotide in an array having a common length of 4–8 nucleotides, and having the same known central base sequence flanked on one or both sides by a further number of bases, the number of bases on any one side of the central sequence being common to all oligonucleotides in an array, all possible flanking base sequences being represented in an array;
   b) contacting the duplex-containing RNA with an RNAse to cleave the duplex-containing RNA, and
   c) measuring the kinetics of cleavage.

2. A method according to claim 1, wherein the RNAse is RNAse H.

3. A method according to claim 1, wherein a label is attached at a site on the RNA such that, as measured along the RNA chain, the site at which cleavage of the RNA occurs is situated between the solid support and the site at which the label is attached.

4. A method according the claim 3, wherein measuring the kinetics of cleavage comprises stopping the cleavage after a fixed period of time, removing cleaved RNA and measuring the remaining quantity of labeled RNA.

5. A method according to claim 3, wherein measuring the kinetics of cleavage comprises recording in real time the loss of a signal produced by the labeled RNA.

6. A method according to claim 5, wherein the RNA is labeled with a radiolabel, the RNA is immobilized on a scintillant-containing surface, and the loss of scintillation is recorded.

7. A method according to claim 6, wherein the radiolabel comprises $^{33}$P.

8. A method according to claim 5, wherein the RNA is labeled with a particulate label or a fluorescent label, an evanescent wave is generated in the proximity of the labeled RNA and the loss of scattering of the evanescent wave by the particulate label or loss of fluorescence of the fluorescent label is recorded.

9. A method according to claim 8, wherein the particulate label comprises gold or selenium.

10. A method according to claim 9, wherein the central base sequence comprises 4–6 nucleotides.

11. A method according to claim 10, wherein the RNA is contacted with a set of arrays, each array in the set having a different known central base sequence of a common length, the set comprising arrays representing all possible central base sequences of that common length.

12. A method according to claim 11, wherein the oligonucleotides are chimeric.

13. A method according to claim 12, wherein the oligonucleotides comprise modified nucleic acids to ensure that the melting points of correctly hybridized oligonucleotides are similar to each other and are greater than the melting points of incorrectly hybridized oligonucleotide.

14. A kit for identifying a functional antisense agent, which kit comprises:
   a) one or more arrays of oligonucleotide, each oligonucleotide in an array having a common length of 4–8 nucleotides, and having the same known central base sequence flanked on one or both sides of a further number of bases, the number of bases on any side of the central sequence being common to all oligonucleotides in an array, all possible flanking base sequences being represented in an array;
   b) an RNAse, and
   c) a means for generating a signal for measuring the kinetics of cleavage of a duplex-containing RNA.

15. A kit according to claim 14, in which the RNAse is RNAse H.

16. A kit according to claim 14, wherein the means for generating a signal comprises a scintillant-containing surface for immobilization of the RNA.

17. A kit according to claim 14, wherein the means for generating a signal comprises an optical waveguide for producing an evanescent wave.

18. A kit according to any of claim 14, wherein the central base sequence comprises 4–6 nucleotides.

19. A kit according to any of claim 14, wherein the kit comprises a set of arrays, each array in the set having a different known central base sequence of a common length, the set comprising arrays representing all possible central base sequences of that common length.

20. A kit according to any of claim 14, in which the oligonucleotides are chimeric.

21. A kit according to any of claim 14, wherein the oligonucleotides comprise modified nucleic acids to ensure that the melting points of correctly hybridized oligonucleotides are similar to each other and are greater than the melting points of incorrectly hybridized oligonucleotides.

* * * * *